United States Patent [19]

Meyer et al.

[11] Patent Number: 4,608,433

[45] Date of Patent: * Aug. 26, 1986

[54] INERT MONOVALENT HYDROCARBON TERMINATED POLYSULFIDE POLYMERS

[75] Inventors: Victor E. Meyer; Thomas E. Dergazarian, both of Midland, Mich.

[73] Assignee: The Dow Chemical Company, Midland, Mich.

[*] Notice: The portion of the term of this patent subsequent to Mar. 20, 2001 has been disclaimed.

[21] Appl. No.: 758,235

[22] Filed: Jul. 24, 1985

Related U.S. Application Data

[63] Continuation-in-part of Ser. No. 552,235, Nov. 16, 1983, abandoned, which is a continuation-in-part of Ser. No. 426,559, Sep. 29, 1982, Pat. No. 4,438,259, which is a continuation-in-part of Ser. No. 339,820, Jan. 18, 1982, abandoned.

[51] Int. Cl.$^4$ ............................................. C08G 75/14
[52] U.S. Cl. .................................... 528/388; 523/122; 523/264; 523/265; 568/23; 568/25; 568/38; 568/46; 568/50; 524/264; 524/265
[58] Field of Search ............... 528/388; 523/122, 265, 523/264; 568/25, 23, 38, 46, 50; 524/264, 265

[56] References Cited

U.S. PATENT DOCUMENTS

| | | | |
|---|---|---|---|
| 2,349,191 | 5/1944 | Olin et al. | 568/25 |
| 2,466,963 | 4/1949 | Patrick et al. | 528/387 |
| 2,986,582 | 5/1961 | Martin et al. | 528/388 |
| 3,367,975 | 2/1968 | Ligget | 528/388 |
| 3,907,899 | 9/1975 | Curran | 568/25 |
| 3,968,264 | 7/1976 | Winter et al. | 568/25 |
| 4,438,259 | 3/1984 | Meyer et al. | 528/388 |

*Primary Examiner*—Melvyn I. Marquis

[57] ABSTRACT

Disclosed herein are inert monovalent hydrocarbon terminated polysulfide copolymers having the general structure

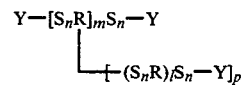

wherein n is an integer from about 2 to about 8, l is zero or a positive integer, m is a positive integer, each R is independently an organic polyradical with the radicals residing on carbon atoms, p is zero or a positive integer which is the difference between the number of radicals on R and 2, and each Y is a terminal substituent that is an inert monovalent hydrocarbon radical.

14 Claims, No Drawings

INERT MONOVALENT HYDROCARBON TERMINATED POLYSULFIDE POLYMERS

CROSS-REFERENCE TO RELATED APPLICATIONS

This application is a continuation-in-part of copending application Ser. No. 552,235, filed Nov. 16, 1983, now abandoned, which is a continuation-in-part of copending application Ser. No. 426,559, filed Sept. 29, 1982, which issued as U.S. Pat. No. 4,438,259, Mar. 20, 1984, which is a continuation-in-part of Ser. No. 339,820 filed Jan. 18, 1982, now abandoned.

BACKGROUND OF THE INVENTION

This invention relates to polysulfide polymers.

Polysulfide polymers are well-known and have been used commercially for many years. See, for example, U.S. Pat. Nos. 1,890,191 and 2,466,963. Such polysulfide polymers are prepared by copolymerizing metal polysulfides and polyfunctional aliphatic hydrocarbons such as ethylene dichloride, 1,2,3-trichloropropane and bis 2-chloroethyl formal. A very high molecular weight rubber is thereby formed, which is then cleaved with sodium hydrogen sulfide and sodium sulfite to yield a lower molecular weight mercaptan-terminated polymer. Although these mercaptan-terminated polymers may be cured by the use of oxidants such as metal oxides to form rubbers with many desirable properties, the mercaptan end groups of these polymers impart a strong, disagreeable odor which limits the practical utility of these polymers.

Grotenhuis et al. disclose in U.S. Pat. No. 2,445,191 that, in order to increase the resistance of polysulfides to cold flow, unsaturated aliphatic compounds may be incorporated into the copolymer such that there is one carbon-carbon double bond for each 100 to 300 carbon atoms. Grotenhuis further notes that a monosubstituted aliphatic compound may be employed to limit the molecular weight of the copolymers. However, the use of such copolymers has not proven commercially practical because said copolymers do not cure well.

Styrene is also known to react with sulfur to produce a high molecular weight polymer, but it rapidly depolymerizes to give 2,4-diphenylthiophene. See Blight et al., Adv. Chem. Ser. 165 13 (1978).

The copolymerization of bis(p-vinylbenzyl)disulfide with styrene and divinylbenzene to form a crosslinked polymer is reported by Wulff and Schulze in Angew Chem. Int. Ed. Engl. Vol. 17, pp. 537-80 (1978). The disulfide linkages are then reduced to mercaptan groups having a predetermined stereochemical relationship. Again, the presence of mercaptan groups imparts an undesirable odor to the crosslinked polymer, greatly limiting its utility.

In view of the deficiencies of previously known polysulfide resins, it is highly desirable to produce a noncurable polysulfide material which is substantially free of offensive odors.

SUMMARY OF THE INVENTION

This invention is a polysulfide polymer which has reduced odor. Generally, the polymers of the present invention are polysulfide polymers having the general structure:

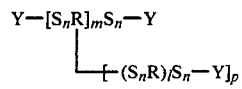

wherein each R is independently a polyvalent organic polyradical with each valence residing on a carbon atom; each Y is a terminal substituent that is an inert monovalent hydrocarbon radical; l and m are independently zero or a positive integer; n is a number from about 2 to about 8 ; and p is zero or a positive integer which is the difference between the valence of R and two.

In a preferred embodiment, the Y terminal substituents are an organic group which is not capable of engaging in a curing reaction (hereinafter a noncrosslinking group), or a mixture of such noncrosslinking group and a (vinylaryl)alkyl group, provided that the proportion of Y substituents which are (vinylaryl)alkyl, is such that the polysulfide polymer is not capable of being cured to a material which does not cold flow.

In another aspect, this invention is a process by which polysulfide polymers are produced wherein desirable properties, i.e., molecular weight, curing properties and branching, are selectively imparted to the polymers. Said process comprises reacting a polysulfide salt of an alkali or alkaline earth metal with an inert monovalent hydrocarbon compound as described hereinafter and at least one inertly substituted polyfunctional organic compound having a plurality of negatively charged functionalities which will split off upon reacting with the metal polysulfide.

DETAILED DESCRIPTION OF THE INVENTION

The inert monovalent hydrocarbon terminated polysulfides of this invention are advantageously produced by the reaction of a metal polysulfide and an inert monovalent hydrocarbon compound having a negatively charged functionality which will split off upon reacting with the metal polysulfide. Metal polysulfides useful in the practice of this invention are soluble polysulfides of a mono- or divalent metal cation which forms a bond with the polysulfide which is primarily ionic in character, i.e. dissociates in water. Particularly useful metal polysulfides are those of calcium, magnesium, lithium, potassium and sodium. Of these, sodium polysulfides are most preferred on the basis of cost and availability.

Said metal polysulfides are prepared by reacting a dissolved metal monosulfide with elemental sulfur and refluxing the mixture to form the desired polysulfide. Alternately, the desired polysulfides are prepared by reacting anhydrous metal sulfides with molten sulfur or by reacting aqueous sodium hydroxide with elemental sulfur. See "Encyclopedia of Chemical Technology," 2d Ed., V. 16, page 255. The process by which the metal polysulfides are generated is a matter of choice to the practitioner of this invention, and should not be construed as critical to the practice of this invention.

The number of sulfur atoms in the polysulfide chain is referred to in the art as the sulfur "rank." The rank of the polysulfide chains is controlled by varying the proportions of the metal sulfide and elemental sulfur employed to form the metal polysulfide. By increasing the proportion of elemental sulfur to the metal sulfide, the average rank of the resulting polysulfide is increased. In the formation of the polysulfide by the reaction of NaOH with elemental sulfur, longer sulfur chains are formed by increasing the temperature at which the reaction is carried out. However, precise control of the sulfur rank is not achieved by any of these processes and the polysulfide chains so produced will have varying ranks. Thus, the "rank" of the sulfur chains produced represents only a number average of the actual individual ranks, and it is understood that said actual individual ranks will vary, usually between 2 to about 8, with the majority of the polysulfide chains having ranks within one of the designated rank. Thus, a polysulfide with a designated sulfur rank of 4 will have individual polysulfide chains having from 2 to about 8 sulfur atoms, with most of the polysulfide chains having 3, 4 or 5 sulfur atoms. In the polymers of this invention, the sulfur rank is in the range from about 2 to 8, with 2 to 4 being preferred.

In making the polysulfides of this invention, the metal polysulfide is reacted with an inert monovalent hydrocarbon compound which contains a negatively charged functionality which will split off upon reacting with the metal polysulfide in the reaction mixture. By inert is meant that the monovalent hydrocarbon compound contains no substituent group which chemically reacts under the conditions of the polymerization reaction. Exemplary inert substituents include, for example, alkyl groups. A wide variety of inert monovalent hydrocarbon compounds are usefully employed herein. The inert monovalent hydrocarbon compound may be, for example, an alkyl halide or sulfate, particularly a $C_2$–$C_{18}$ alkyl chloride or bromide. Halogenated or sulfated cycloalkyl compounds are useful herein, as well as (aryl)alkyl halides, sulfates and the like. Of the foregoing, (aryl)alkyl halides are preferred.

The inert monovalent hydrocarbon compound is preferably one which is not capable of engaging in a curing reaction, or a mixture of such a noncrosslinking compound with a (vinylaryl)alkyl halide or other compound which reacts with the metal polysulfide to form a terminal (vinylaryl)alkyl substituent. When such a mixture of inert monovalent hydrocarbon compounds is employed, the proportion of such mixture employed is preferably such that the resulting polysulfide polymer is incapable of curing to a material which does not cold flow. In other words, for the purposes of this invention, it is preferred to have a polysulfide which is incapable of curing to form a highly crosslinked material. Of course, in evaluating the curing behavior of the polysulfide, such behavior refers to the curing characteristics of neat polysulfide elastomers. The inclusion of diverse additives may affect the mechanical properties of the polysulfide material such that even those containing very small amounts of (vinylaryl)alkyl terminal substituents do not cold flow.

Most preferably, the inert monovalent hydrocarbon compound is an unsubstituted or inertly substituted benzyl halide, or a mixture thereof with an unsubstituted or inertly substituted vinylbenzyl halide.

Polysulfide polymers are formed by introducing, in addition to the inert monovalent hydrocarbon compound, an organic compound having a plurality of negatively charged functionalities attached to an aliphatic or cycloaliphatic carbon atoms, which functionalities will split off upon reacting with the metal sulfide in the reaction mixture. As used herein, the term "negatively charged functionality" means a functional group which will split off on reacting with the metal polysulfide to form an anionic species in solution. The functional group is not necessarily ionically bonded to the aliphatic hydrocarbon or (vinylaryl)alkyl compound, and, in fact, is generally covalently bonded thereto. The condensation polymerization of polysulfides and polyfunctional organic compounds are well known in the art and is first described in U.S. Pat. No. 1,890,191 to Patrick. Suitable polyfunctional compounds include alkyl dihalides, disulfates, diacetates and the like which will polymerize with the polysulfide and the inert monovalent hydrocarbon compound to form a linear polymer represented by the formula:

wherein m is a positive integer, n and Y are as defined hereinbefore and $R_a$ represents an organic diradical, with each valence residing on a carbon atom, which is the residue of the difunctional hydrocarbon after the splitting off of the negatively charged functionalities. In general, chlorides are preferred as the negatively charged functional group due to the facility of their reaction with metal polysulfides, their relatively low cost and high availability. The $R_a$ group, and correspondingly, the polyfunctional organic compound, may further contain substituents which are inert under the conditions of the polymerization reaction and may further incorporate linkages such as ether, sulfide, alkene or arylene into the chain. In general, those polyfunctional monomers previously known to react with metal polysulfides to form polymers therewith are also suitably employed in this invention. Preferred polyfunctional monomers include dichloroethane, 1,2,3-trichloropropane, bis-2-chloroethyl formal, bis-4-chlorobutyl ether, bis-4-chlorobutyl formal and 1,3-dichloro-2-propanol. Other polyfunctional monomers, which are illustrative of the wide scope of monomers suitably employed herein include, for example, bis(4-chloromethyl)phenyl ether, bis(4-chloroacetyl)phenyl ether, 2,5,-di(chloromethyl)1,4-dioxane and diethylene glycol bis(chloroacetate), propylene dichloride, and 1,4-dichloro-2-butene.

Trifunctional, tetrafunctional and pentafunctional organic compounds, such as 1,2,3-trichloropropane and the like, may be employed in conjunction with difunctional hydrocarbons and will polymerize with the polysulfide and the (vinylaryl)alkyl compound to form a branched polymer as represented by the general structure:

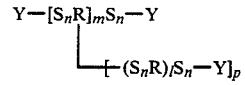

wherein l and m are positive integers, n and Y are as defined hereinbefore, each R is independently a polyvalent organic polyradical with each valence residing on a carbon atom, and p is zero or a positive number which is the difference between the valence of R and two. It is noted that each R is the residue formed by the splitting off of the negatively charged functionalities from the respective difunctional and polyfunctional hydrocarbons.

The amount and degree of branching of the polymer is selectively determined by the choice and relative proportion of the organic monomers employed in the reaction. By polymerizing polysulfides with a mixture of difunctional and tri-, tetra- or pentafunctional monomers, a branched chain may be formed as desired. In general, suitably branched polysulfide polymers are produced by employing from 90 to 99.5 weight percent of a difunctional monomer and from 10 to 0.5 weight percent of a monomer having at least three functionalities, said percentages being based on the total weight of all the polyfunctional monomers employed in the reaction. If higher modulus and lower cold flow in the cured polymer are desired, from about 2 to 10 weight percent, preferably from 3 to 5 weight percent, of a monomer having at least three functionalities is employed, said percentages being based on the total weight of all the polyfunctional monomers employed in the reaction. If the polymer is to be employed as a sealant, from about 0.5 to about 4 weight percent of a monomer having at least 3 functionalities is beneficially employed.

The polyfunctional monomer is chosen such that the polymer produced therefrom has the desired physical properties. Many of the beneficial properties of polysulfide polymers, such as resistance to oxygen permeation, water, ultraviolet light and solvents are generally attributable to the polysulfide segments of the polymer. When the sulfur link is three or more, the sulfur linkages also impart flexibility to the polymer. By contrast, properties such as high elongation, flexibility, and increased solubility may be selectively imparted to the polymers primarily by the organic segments. Thus, the properties of the polymers of this invention can be selectively determined by the choice of polyvalent organic compound and the rank of the polysulfide segments. For example, a high sulfur polymer can be produced by employing low molecular weight organic compounds, such as bis-2-chloromethyl formal, 1,2,3-trichloropropane or ethylene dichloride. Similarly, polysulfides of varying rank may be employed to selectively vary the carbon to sulfur ratio in the polymeric chain.

The reaction is suitably carried out by heating the aqueous polysulfide solution from about 25° to about 90° C., preferably from about 50° to about 80° C., and adding the polyvalent organic compound and the inert monovalent hydrocarbon compound over a period of about 5 minutes to 2 hours. The mixture is then heated at 25° to 90° C., preferably from about 50° to about 80° C., for about 1 to 3 hours to form the desired inert monovalent hydrocarbon terminated polysulfide.

Because the metal polysulfide is ordinarily contained in an aqueous phase, the organic reactants are advantageously intermixed with the aqueous phase to facilitate the reaction. Said intermixing may be achieved by adjusting the density of the aqueous phase to approximate that of the organic phase or by forming an emulsion. An emulsion can be created by the addition of a suspending agent such as magnesium hydroxide in conjunction with a surfactant such as sodium lauryl sulfate or other organic surfactants such as alkylated sulfonated phenyl ethers. The suspended organic phase thus reacts more readily with the dissolved polysulfide to form the desired inert monovalent hydrocarbon terminated polysulfide. Following the reaction, the product is recovered by breaking the emulsion. This may be done by adding water and acid to adjust the pH to about 2 to 6, preferably from about 3 to 5. Alternatively, the product may be recovered by adding an organic solvent such as acetone, or by mechanical means such as centrifugation, or combinations thereof. Means for recovering organic products from an emulsion are well known in the art and are not considered critical to the invention. It may be preferred, for some applications, not to recover the polymer from the emulsion, but instead employ the polymer in the form of a latex.

By varying the proportion of the inert monovalent hydrocarbon compound employed in the polymerization reaction, the molecular weight of the polymer is controlled. The molecular weight of the polymer formed according to this invention increases as the proportion of the inert monovalent hydrocarbon compound is decreased. Thus, non-curable polymers of the desired molecular weight may be produced in a single reaction. The polymers of this invention have a theoretical molecular weight, as calculated from the relative proportions of the reactants employed, of at least about 490, preferably from about 3,000 to about 200,000, more preferably from about 3,000 to about 25,000. As molecular weight control in previously known processes for producing polysulfide resins cannot be achieved during the polymerization reaction, said control of the molecular weight represents a significant step forward in the art. In addition, control of the molecular weight in the polymerization reaction obviates the need for the cleavage step required in the formation of previously known polysulfide resins. Because the cleavage step in the prior art introduces terminal mercaptan substituents to the resins thus produced, the elimination of this step produces a polymer free of the objectionable odors of previously known polysulfide resins.

The polysulfide materials of this invention have a general structure as represented by the formula

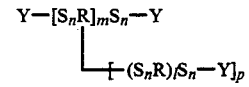

wherein 1, m, n, R and Y are as defined hereinbefore. In the preferred embodiment, a sufficient proportion of Y are noncrosslinking such that the polymer is not capable of curing to a material that does not cold flow. It is, of course, understood that the above structure represents only an average structure wherever a mixture of noncrosslinking terminal substituents and (vinylaryl)alkyl terminal substituents are present. Species having no (vinylaryl)alkyl terminal groups will probably form in this reaction, as well as species in which all terminal substituents are (vinylaryl)alkyl, their relative proportions thereof being determined by the relative proportions and reactivity of the (vinylaryl)alkyl compound and the noncrosslinking inert monovalent hydrocarbon compound employed in the reaction mixture. It is preferred that the reactivity of the (vinylaryl)alkyl compound and the noncrosslinking inert monovalent hydrocarbon compound in the polymeric reaction be roughly comparable. For this reason, benzyl chloride is highly preferred as the noncrosslinking inert monovalent hydrocarbon compound if vinylbenzyl chloride is employed as the (vinylaryl)alkyl compound.

Because the properties of the polymers are readily controlled by varying the type and proportions of the reactants, the polymers of this invention are readily adapted to a wide variety of uses. Said polymers are useful coatings for materials such as wood, metal, glass, concrete and synthetic fibers as well as for absorbent materials such as textiles, paper, leather and the like. In addition, articles such as hoses, sheets, rollers, tanks, gaskets, wire insulation and the like may also be fashioned from said polymers. Said polymers are also useful as components in caulking and sealing compositions.

Due to their low odor, the polymers of this invention may be used in household and other populated environments where the odor of previously known polysulfide polymers precludes their use.

Due to their good adhesion to glass and resistance to solvents, water and gases, the polymers of this invention have particular applications as sealants and in caulking compositions. Low modulus, highly extensible polysulfide polymers of this invention, i.e., those which are lightly branched and/or lightly crosslinked when cured, are most beneficially employed in sealant compositions. Plasticizers, fillers, pigments and the like may be beneficially employed in the sealant compositions according to this invention. Although the polymers of this invention adhere well to glass, adhesion is further increased by the incorporation of about 0.1 to about 5 weight percent of a coupling agent. Exemplary coupling agents include organosilane coupling agents such as mercaptopropyltrimethoxysilane and

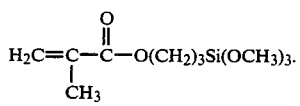

The sealants of the present invention exhibit excellent water and solvent resistance and gas impermeance.

Water-resistant caulking compositions are also prepared from the polymers of this invention. Polysulfide polymers of this invention exhibit high water-resistance, good adhesion, minimal cold flow when formulated and are especially suitable for use in non-hardening caulking compositions. In addition to their excellent mechanical properties, the polymers of this invention do not support fungal growth. For this reason, the polymers of this invention have an advantage over previously known caulking compositions, which must usually be compounded with a fungicide to inhibit fungal growth thereon.

The polysulfides of this invention are also excellent as plasticizers for various organic elastomers which contain residual unsaturation. Surprisingly, these polysulfide polymers are compatible with such organic elastomers, i.e., they form blends with the organic elastomer, which blends do not phase separate. The polysulfides of this invention are even compatible with butyl rubbers, with which conventional polysulfide polymers are usually incompatible.

In addition to plasticizing said organic elastomers, the polysulfides of this invention also vulcanize these rubbers. Thus, blends of these polysulfide polymers and an organic elastomer generally do not require the addition of either an additional plasticizer or an additional vulcanizer.

To further extend the usefulness of the polymers of this invention, they may be compounded with various inert fillers such as fibers, wood flour, carbon black, asbestos, glass, inorganic pigments and the like.

The following examples are illustrative and are not intended to limit the scope of the invention in any way. All percentages are by weight unless specifically noted otherwise.

EXAMPLE 1

A 96 g portion of disodium sulfide nonahydrate is dissolved into about 200 ml water in a flask equipped with an agitator, a reflux condenser and a means for temperature control. A 38.5 g portion of precipitated sulfur is added and heated at reflux for 1 hour to produce a disodium tetrasulfide. The mixture is then cooled to 70° C. and 18.2 g hydrated magnesium chloride, 7.2 g sodium hydroxide, 10 g surfactant solution and 100 ml water are added. While maintaining this reaction mixture at 70° C., 2.30 g benzyl chloride and 38.7 g ethylene dichloride are added over a 1 hour period, followed by heating at reflux for 1 hour. The emulsion is then broken by the addition of dilute acid solution. The resulting polymer is linear and has terminal benzyl substituents. This polymer is designated as Polysulfide Sample No. A.

EXAMPLE 2

Following the general procedure described in Example 1, an inert monovalent hydrocarbon terminated polysulfide polymer is prepared from:

96 g $Na_2S$
38.5 g sulfur
0.08 g vinylbenzyl chloride
11.75 g benzyl chloride
34.3 g ethylene dichloride
0.894 g 1,3 dichloro-2-propanol The resulting polymer is linear and has a theoretical molecular weight of about 1,500. The terminal substituents are predominately benzyl groups, with a very small proportion of vinylbenzyl substituents being present. Heating this material to about 150° C. to 120° C. does not promote any significant curing.

EXAMPLE 3

A curable polysulfide (Polysulfide Sample No. B) is prepared, according to the general procedure described in Example 1, from 1,441 g $Na_2S.9$ $H_2O$, 577.2 g sulfur, 14.6 g vinylbenzyl chloride, 12.1 g benzylchloride and 584.3 g ethylene dichloride. This polymer has a molecular weight of 10,000 and cures to a material which does not cold flow.

Sealant Formulation Nos. 3A and 3B are prepared from Polysulfide Sample Nos. A (Example 1) and B by blending the following components on a Brabender mixer at 125° C.

|  | Sealant No. 3A (parts) | Sealant No. 3B (parts) |
| --- | --- | --- |
| Polysulfide Sample No. A (Example 1) | 100 | — |
| Polysulfide Sample No. B | — | 100 |
| Polyisobutylene | 5 | 5 |
| Kraton 1107[1] | 10 | 10 |
| Carbon Black N762[2] | 30 | 30 |
| ZnO | 2.5 | 2.5 |

[1]A styrene/isoprene/styrene block copolymer having a melt index of 9, available from the Shell Chemical Company
[2]Cabot Corporation Tensile bars of ⅛" thickness are prepared from each of Sealant No. 1 and 2. These bars are tested in an Instron Tensile Tester at 25° C. The jaws of the Instron are originally set 1" apart and are operated at a cross-head speed of 20" per minute until the bars are elongated to 9". Sealant No. 1 exhibited a peak tensile stress of 12.1 psi and a tensile at 800% elongation of 2.7 psi. Sealant No. 2 exhibited a peak tensile stress of 51.0 psi and a tensile at 800% elongation of 19.4 psi. These differences in tensile between the two sealant formulations clearly demonstrate the curing which occurs when the polysulfide contains vinylbenzyl-terminal substituents.

EXAMPLE 4

Two sealant formulations (designated herein Sealant No. 4A and 4B) are prepared from Polysulfide No. 2 of Example 3, by blending the following components in a Brabender mixer at about 118° C.

|  | Sealant No. 4A (parts) | Sealant No. 4B (Parts) |
|---|---|---|
| Polysulfide Sample No. 2 | 100 | 100 |
| Polyisobutylene | 5 | 5 |
| Kraton 1107[1] | 10 | 10 |
| Carbon Black N762[2] | 20 | 20 |
| ZnO | 2.5 | 2.5 |
| Benzyltetrasulfide | 0 | ~1.4 |

[1] A styrene/isoprene/styrene block copolymer having a melt index of 9, available from the Shell Chemical Company
[2] Cabot Corporation In order to demonstrate the plasticizing effect of the noncrosslinking inert monovalent hydrocarbon terminal groups, the torque exerted by the blended sealant on the Brabender Mixer is measured at 90° C. The torque exerted by Sealant No. 4A is 424 meter·grams at 100° C. and 654 meter at 90° C. By contrast, the plasticized Sealant No. 4B exert only 133 meter·grams of torque at 100° C. and 217 meter·grams of torque at 90° C. Thus, the effectiveness of the noncurable polysulfide of this invention as a plasticizer is clearly demonstrated.

What is claimed is:

1. A polysulfide polymer having a molecular weight from about 3,000 to about 100,000, as represented by the general structure

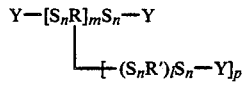

wherein R and R' at each occurrence are independently polyvalent organic polyradicals with each valence residing on a carbon atom; each Y is a terminal substituent that is an inert monovalent hydrocarbon radical; 1 is zero or a positive integer; m is a positive integer; n is a number from about 2 to about 8; and p is zero or a positive integer which is the difference between the valence of R and two.

2. A polymer as in claim 1 wherein each Y is independently a (vinylaryl)alkyl substituent or an organic group which is not capable of engaging in a curing reaction, provided that fewer than 10 percent by number of the Y substituents are (vinylaryl)alkyl.

3. A polymer as in claim 2 wherein said Y substituent is an unsubstituted or inertly substituted (aryl)alkyl, or cycloalkyl group.

4. A polymer as in claim 2 wherein each Y substituent is an (aryl)alkyl or (vinylaryl)alkyl group.

5. A polymer as in claim 4 wherein each Y substituent is vinylbenzyl or benzyl.

6. A polymer as in claim 2 wherein each R is independently an aliphatic diradical.

7. A polymer as in claim 2 wherein each R is independently an alkylene diradical, bis(4-chloromethyl)phenyl ether, bis-(4-chloroacetyl)phenyl ether, 2,5-di(-chloromethyl)-1,4,-dioxane or diethylene glycol bis(-chloroacetate).

8. A polymer as in claim 2 wherein each R is selected such that from about 90 to about 99.5 weight percent, based on the combined weight of all the R groups, of the R groups are organic diradicals and from about 10 to about 0.5 weight percent of the R groups have at least 3 valences.

9. A polymer as in claim 2 having a molecular weight from about 3,000 to 25,000.

10. A process for making polysulfide polymers, comprising reacting a mixture comprising an alkali-or alkaline earth polysulfide, at least one unsubstituted or inertly substituted polyfunctional organic compound having a plurality of negatively charged functionalities attached to an aliphatic or alicyclic carbon atom, which functionalities will split off upon reacting with said alkali or alkaline earth polysulfide, and an inert monovalent hydrocarbon compound having a negatively charged functionality which will split off upon reacting with said alkali or alkaline earth polysulfide.

11. A process as in claim 10 wherein said inert monovalent hydrocarbon compound comprises a (vinylaryl)alkyl halide and a noncrosslinking inert monovalent hydrocarbon compound provided that a sufficient proportion of the terminal substituents of the polymer so made are not (vinylaryl)alkyl that the polymer is incapable of curing to a material which does not cold flow.

12. A process as in claim 11 wherein the reaction is carried out at a temperature from about 25° C. to about 90° C.

13. A process as in claim 11 wherein the reaction is carried out in an emulsion.

14. The process of claim 12 wherein the inert monovalent hydrocarbon compound comprises a mixture of a vinylbenzylhalide and a benzyl halide.

* * * * *